(12) United States Patent
Seo et al.

(10) Patent No.: US 8,021,652 B2
(45) Date of Patent: Sep. 20, 2011

(54) BIODEGRADABLE BRANCHED POLYLACTIDE DERIVATIVES CAPABLE OF FORMING POLYMERIC MICELLES, AND THEIR PREPARATION METHOD AND USE

(75) Inventors: Min-Hyo Seo, Daejeon (KR); Bong-Oh Kim, Daejeon (KR); In-Ja Choi, Daejeon (KR); Myung-Seob Shim, Seoul (KR)

(73) Assignee: Samyang Corporation, Seoul (KR)

( * ) Notice: Subject to any disclaimer, the term of this patent is extended or adjusted under 35 U.S.C. 154(b) by 1176 days.

(21) Appl. No.: 10/554,637

(22) PCT Filed: Dec. 3, 2004

(86) PCT No.: PCT/KR2004/003174
§ 371 (c)(1),
(2), (4) Date: Oct. 27, 2005

(87) PCT Pub. No.: WO2005/054333
PCT Pub. Date: Jun. 16, 2005

(65) Prior Publication Data
US 2007/0003625 A1      Jan. 4, 2007

(30) Foreign Application Priority Data
Dec. 4, 2003   (KR) .................. 10-2003-0087459

(51) Int. Cl.
*A61K 31/765*   (2006.01)

(52) U.S. Cl. .................................................. 424/78.37

(58) Field of Classification Search ............... 424/78.37, 424/78.17, 78.08
See application file for complete search history.

(56) References Cited

U.S. PATENT DOCUMENTS

| 5,929,177 A | 7/1999 | Kataoka et al. |
| 2004/0091573 A1* | 5/2004 | Sodergard .................. 426/3 |

FOREIGN PATENT DOCUMENTS

| JP | 10-110019 A | 4/1998 |
| KR | 99-14879 A | 2/1999 |
| KR | 2003-32896 A | 4/2003 |
| KR | 2003-32897 A | 4/2003 |
| KR | 2003-45611 A | 6/2003 |
| WO | WO-03/033593 A1 | 4/2003 |

OTHER PUBLICATIONS

Lee et al., 2001, "Synthesis and Degradation of End-Group-Functionalized Polylactide", Journal of Polymer Science: Part A: Polymer Chemistry, vol. 39, 973-985.*

Li et al., "Synthesis, characteristics and in vitro degradation of star-block copolymer consisting of L-lactide, glycolide and branched multi-arm poly(ethylene oxide)" Polymer 39, 1998, pp. 4421-4427.

* cited by examiner

*Primary Examiner* — Michael G Hartley
*Assistant Examiner* — James Rogers
(74) *Attorney, Agent, or Firm* — Birch, Stewart, Kolasch & Birch, LLP

(57) ABSTRACT

The present invention relates to a biodegradable branched polylactic acid derivative of formula 1, and preparation method and use thereof: <formula 1> $1\text{-}(R\text{—}X)_n$ wherein each of X, R, I and n is defined as in the detailed description.

12 Claims, 4 Drawing Sheets

BIODEGRADABLE BRANCHED POLYLACTIDE DERIVATIVES CAPABLE OF FORMING POLYMERIC MICELLES, AND THEIR PREPARATION METHOD AND USE

TECHNICAL FIELD

This invention relates to a branched polylactic acid derivative capable of forming polymeric micelles in aqueous solution of pH 4 or more, and a preparation method and use thereof, wherein the branched polylactic acid derivative contains carboxy group or carboxy alkali metal salt group in the terminal of polymer chain.

BACKGROUND ART

Solubilization of poorly water-soluble drugs is essentially required to deliver the drugs into the body by oral or parenteral administration. Drug delivery systems are designed to maximize efficacy and effects of drugs and to minimize side effects of drugs. In particular, efficacy of poorly water-soluble drugs that are not easily dissolved in water can be enhanced remarkably by solubilizing by drug delivery systems. Most drugs, after administration, must have a constant plasma concentration in order to provide desired pharmacological effects. In particular, drugs with short half-life should be administered frequently to achieve effective plasma concentration, and be slowly released from the preparation to maintain sustained pharmacological effects. To do so, micelles formed by polymer used for solublizing poorly water-soluble drugs should be more stable, for which the critical micelle concentration (CMC) should be low, and the affinity between poorly water-soluble drugs having high hydrophobicity and hydrophobic block of copolymer should be increased.

The unit size of droplet of micelles formed by surfactant can be controlled to several nm to several tens μm, and so the micelles are in the form finely dispersed in solutions since poorly water-soluble drugs solution are contained in the droplet. Thus, the method to form micelles to solublize poorly water-soluble is regarded as most preferable, and so among the solubilization methods using micelles, use of surfactant is one of key technologies.

Recently, as a method for solubilizing and delivering poorly water-soluble drugs, there have been many studies for methods delivering poorly water-soluble drugs by entrapping the drugs into the core of micelles or nanoparticles formed of amphiphilic block copolymer consisted of hydrophilic polymer and hydrophobic polymer.

For example, U.S. Pat. No. 5,543,158 discloses a dosage form that drug is entrapped into nanoparticle formed of amphiphilic block copolymer consisted of a hydrophilic polyethylene glycol block and a hydrophobic copolymer of polylactide and polyglycolide block. Also, U.S. Pat. No. 6,322,805 discloses a technology to solubilize poorly water-soluble drugs by using biodegradable polymers comprised of monomethoxypolyethylene glycol and polylactide as an amphiphilic diblock copolymer, wherein poorly water-soluble drugs is physically contained into core of micelles and solubilized in aqueous solution without chemical combination.

As shown above, prior poorly water-soluble drugs required hydrophilic polymer such as polyethyleneglycol, etc. to have core-shell structure in addition to biodegradable hydrophobic polymer like polyesters. Here, the hydrophilic polymer such as polyethyleneglycol is biocompatible element, but is not completely degraded in human body, while the polyester based hydrophobic polymer can be degraded in human body. Thus, there have been attempts to develop a drug delivery agent of core-shell structure with only bio-degradable polyesters hydrophobic polymer without hydrophilic polymer.

In particular, polylactic acid has very good biocompatibility, and is hydrolyzed into lactic acid harmless to human body. Thus, it has been developed in the form of microsphere, implant agent, etc., by using a characteristic that polymer having molecular weight of 2,000 dalton or more is not soluble in aqueous solution. However, the hydrophobic polymer could not form micelles to solubize poorly water-soluble drugs, and so could not be developed as drug delivery agent for solublizing poorly water-soluble drugs, only with polylactic acid polymer.

Thus, the present inventors have prepared linear polylactic acid derivatives wherein the balance between hydrophilic group and hydrophobic group is adjusted by binding carboxyl group to the terminal of polylactic acid to form polymeric micelles in aqueous solution, and filed the invention as Korean Patent Application No. 2001-64164. However, the polylactic acid derivatives have linear structure that only one molecule of carboxyl group is bound to the terminal, and so the molecular weight of the polylactic acid derivatives capable of forming polymeric micelles in aqueous solution was limited to the range of 2,000 Dalton and less. Also, micelles could not be formed in the higher molecular weight since the derivatives could not be dissolved in aqueous solution. In short, the above polylactic acid derivatives have relatively low molecular weight and cannot entrap the drug in the micelle for a long time due to the poor stability of formed micelles.

Also, Y. Li, et al. discloses that in case of using amphiphilic polymer formed by branched polymer or multi-armed polymer as drug delivery agent, the structural stability of drug delivery agent is enhanced since the polymer has slower biodegradation rate than linear polymer [Polymer, 39, pp. 4421-7(1998)]. This article also used branched polyethyleneglycol as an initiator, and synthesized the branched diblock copolymer by linking mono-polymer or co-polymer such as polylactic acid, polyglycolide and polycaprolactone etc. to each branch. Microparticles or hydrogel containing drug was prepared from these polymers so that drug is released according to the biodegradation rate of polymers. Further, in the U.S. Patent Application Publication No. 2002-0156047, polylactic acid was synthesized and linked with hydrophilic polyethyleneglycol to each of its branches to use as drug delivery agent. This application discloses that the synthesized branched diblock copolymer can effectively entrap hydrophobic drug since the hydrophobic polylactic acid is placed in core region at the middle. However, the drug delivery agent in the above references has a problem that the used hydrophilic polymer is not fully degraded in the human body since the drug delivery agent uses polyethyleneglycol as hydrophilic block of amphiphilic block copolymer.

On the other hand, there is a report to have synthesized branched polymer consisted of only biodegradable polyesters polymer without using polyethyleneglycol. For example, a report shows that pentaerythritol is used as an initiator to synthesize 4-arm branched polycaprolactone, to link maleic anhydride to the 4 hydroxy terminal groups, and to bridge-bind by using UV [M. Lang, et al., J. Appl. Polymer Sci., 86, 2296 (2002)]. Also, there is a report that polyol is used as an initiator to synthesize a branched polylactide, to link methacryloyl chloride to each hydroxy terminal group to synthesize macromer, and then to synthesize porous scaffold by reacting dibenzoyl peroxide [M. Schnabelrauch, Biomaterial Engineering, 19, 295(2002)]. However, these branched polymers have disadvantages that they cannot be used as drug delivery agent since they cannot be solubilzed in aqueous solution due to imbalance between hydrophilic part and hydrophobic part, and that they are not biodegradable in human body since they are cross-linked to improve the mechanical property as medical device.

DETAILED DESCRIPTION OF THE INVENTION

The present inventors prepared branched polylactic acid derivatives having hydrophilic functional group, carboxy group, at each branch, to form polymer micelles of the polylactic acid derivative with increased stability, and found that the branched polylactic acid derivative can form micelles in aqueous solution in high molecular weight and stable micelles can be formed by increasing polymeric molecular weight capable of forming polymer micelles in aqueous solution according to the number of branch, to complete the present invention.

Thus, the object of the present invention is to provide a biodegradable branched polylactic acid derivative which has superior biocompatibility and can form stable polymer micelles in aqueous solution of pH 4 or more.

Another object of the present invention is to provide a preparation method of the above biodegradable branched polylactic acid derivative.

Another object of the present invention is to provide use of the above biodegradable branched polylactic acid derivative as poorly water-soluble drug delivery agent.

CONSTITUTION OF THE INVENTION

Figure 1:
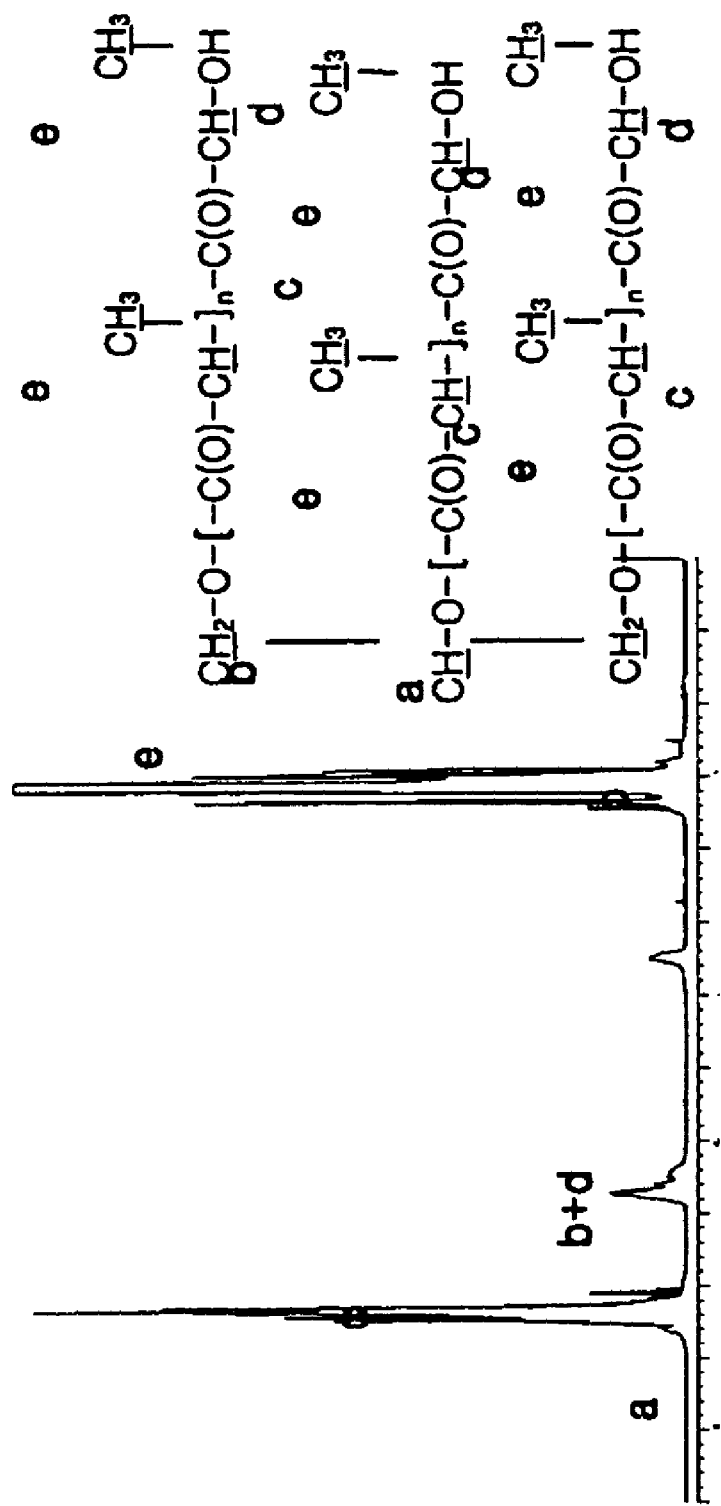
FIG. 1 is $^1$H-NMR spectrum of 3-arm PLA-OH (Preparation Example 1)

First, the present invention relates to a branched polylactic acid derivative of formula 1:

<formula 1> wherein,
R is —[R$_1$]$_k$—[R$_2$]$_m$—,
wherein R$_1$ is —C(=O)—CHZ—O—,
R$_2$ is —C(=O)—CHY—O—, —C(=O)—CH$_2$CH$_2$CH$_2$CH$_2$CH$_2$—O— or —C(=O)—CH$_2$—O—CH$_2$CH$_2$—O—, wherein each of Z and Y is hydrogen, methyl, or phenyl,
k is an integer of 1-30,
m is an integer of 0-30;
X is —C(=O)—(CH$_2$)$_a$—C(=O)—O-M, wherein a is an integer of 0-10, M is hydrogen, sodium, potassium, or lithium;
I is a diol such as ethyleneglycol, propanediol, butanediol, pentanediol, hexanediol etc., or polyol having 3-12 hydroxy group selected from glycerol, erythritol, threitol, pentaerythritol, xylitol, adonitol, sorbitol, mannitol, a disaccharide such as palatinose, maltose monohydrate, maltitol etc., or a trisaccharide such as D-raffinose pentahydrate etc.;
n is an integer of 2-12, and same as the number of hydroxy group that I has.

Second, the present invention relates to a preparation method of the branched polylactic acid derivative, comprising the steps of:
1) polymerizing monomer of lactides in the presence of an initiator and catalyst to obtain a branched polylactic acid;
2) dissolving the branched polylactic acid obtained in step 1) in water-miscibile organic solvent, purifying the branched polylactic acid by adding aqueous solution of pH 7 or more, and drying in vacuum, to obtain powder form of the branched polylactic acid;
3) reacting the branched polylactic acid derivative obtained in step 2) with succinic anhydride or dichloride compound to obtain the branched polylactic acid derivative containing carboxy terminal group; and
4) optionally, adding an alkali metal salt to the branched polylactic acid derivative obtained in step 3) to obtain the branched polylactic acid derivative containing carboxy alkali metal salt terminal group.

Third, the present invention relates to a poorly water-soluble drugs delivery composition containing the above branched polylactic acid derivative.

Forth, the present invention relates to a pharmaceutical composition containing the above branched polylactic acid derivative and the poorly water-soluble drug.

Below, the present invention is described in detail.

R is a branch in the branched polylactic acid derivative of the present invention, and as biodegradable polymer having superior biocompatibility, mono-polymer or copolymer which is one or more selected from the group consisting of lactide, glycolide, caprolactone, 1,4-dioxane-2-one or mandelic acid, or mono-polymer or copolymer selected from polyorthoester, polyanhydride, polyphosphazene, polyamino acid, or polycarbonate. Preferably, R is mono-polymer or copolymer which is one or more selected from the group consisting of lactide, glycolide, caprolactone, 1,4-dioxane-2-one, or mandelic acid. It is preferable that the molecular weight of R is 300-3,000 Dalton, more preferably, 500-1,500 Dalton.

The total molecular weight of the branched polylactic acid derivative of the present invention is a value that multiply the molecular weight of R consisted of one branch by the number of branch. For example, in formula 1, if n is 6, 6-arm branched polylactic acid derivative is obtained, and the total molecular weight is 1,000 Dalton by a number average molecular weight, preferably 3,000 Dalton. In formula 1, n is an integer of 2-12, and thus the number average molecular weight of branched polylactic acid derivative of the present invention is 600-36,000 Dalton, preferably 1,000 Dalton.

As shown above, the branched polylactic acid derivative of the present invention can form stable micelles in aqueous solution due to the increased total molecular weight and stably maintain micelles by solubilizing poorly water-soluble drugs within the micelles.

Also, the branched polylactic acid derivative of the present invention has carboxy group or carboxy alkali metal salt group at each polymer chain terminal of the branch. Preferably, the terminal group of polymer chain is carboxy alkali metal salt group. The carboxy alkali metal salt group forms the branched polylactic acid derivative of sodium, potassium, or lithium monovalent metal ion salt form.

In order for the above polylactic acid derivative to form polymer micelles in aqueous solution, hydrophilic group and hydrophobic group of the polylactic acid derivative should be balanced. In case of linear polylactic acid, there is one carboxy group conducting hydrophilic function, and so the molecular weight capable of forming polymer micelles is 500-2,000 Dalton. The branched polylactic acid derivative of the present invention in which several such linear polylactic acids are linked has carboxy groups conducting hydrophilic function at each branch, thereby increasing hydrophilic part, and to achieve balance with the increased hydrophilic part, hydrophobic part may be increased, too. Thus, to enhance stability the branched polylactic acid derivative of the present invention can form polymer micelles in aqueous solution though the molecular weight of ester part having hydrophobicity is increased. As a result, the branched polylactic acid derivative of the present invention can form micelles with enhanced stability.

As shown in the Example of the present invention, solubility is varied depending on pH in the branched polylactic acid derivative of formula 1. The derivative is completely dissolved in aqueous solution of pH 4 or more, and so can be observed as clear solution state with the naked eye. However, after adjusting pH less than 4, the branched polylactic acid derivative is precipitated (See FIG. 4). Since biodegradable polymer is generally hydrolyzed in pH 10 or more, the branched polylactic acid derivative of the present invention can be used at the range of pH 1-10. Considering that the polymer is biodegradable and is dissolved completely in aqueous solution of pH 4 or more, it is preferable to prepare and use the polymer in the range of pH 4-8.

The branched polylactic acid derivative according to the present invention can be prepared by a method, comprising the steps of:

1) polymerizing monomer of lactides in the presence of an initiator and catalyst to obtain a branched polylactic acid;

2) dissolving the branched polylactic acid obtained in step 1) in water-miscibile organic solvent, purifying the branched polylactic acid by adding aqueous solution of pH 7 or more, and drying in vacuum, to obtain powder form of the branched polylactic acid;

3) reacting the branched polylactic acid derivative obtained in step 2) with succinic anhydride or dichloride compound to obtain the branched polylactic acid derivative containing carboxy terminal group; and 4) adding an alkali metal salt to the branched polylactic acid derivative obtained in step 3) to obtain the branched polylactic acid derivative containing carboxy alkali metal salt terminal group.

In the above preparation method, step 4) can be omitted. In the case, the branched polylactic acid derivative containing carboxy group which is not substituted with metal ion at the terminal is formed.

In the step 1), The diol such as ethyleneglycol, propanediol, butanediol, pentan diol, hexandiol etc. or polyol having 3-12 hydroxy group selected from glycerol, erythritol, threitol, pentaerythritol, xylitol, adonitol, sorbitol, mannitol, a disaccharide such as, palatinose, maltose monohydrate, maltitol etc., or a trisaccharide such as D-raffinose pentahydrate etc., can be used as an initiator. Here, it is possible to synthesize the branched polylactic acid derivative having much more branches if disaccharide or polysaccharides is used as an initiator.

All of these initiators have hydroxy group, and polymer is synthesized when lactide is ring-opening polymerized on this hydroxyl group. That is, polymeric branch number is decided according to the number of hydroxy group of the initiator. Whichever initiator in the above is selected, the branched polylactic acid derivative can be synthesized without change of the reaction procedure. Only, the number of branch is changed.

After quantifying the above initiator, moisture is removed by using vacuum pump at a temperature of about 80° C. Catalyst dissolved in toluene is added thereto. Then, toluene is removed in vacuum condition, and lactide monomer is added thereto, followed by polymerizing the mixture in the temperature range of 100-160° C. under decreased pressure condition of 25-0.1 mmHg for 6-24 hours to obtain the branched polylactic acid. At that time, it is preferable to use catalyst in 0.1 wt % of mononer. Stannous octoate, etc. are catalysts that can be used in step 1).

The molecular weight of the branched polylactic acid derivative of the present invention may be controlled according to the molar ratio of diol or polyol initiator and monomer participating in the reaction. When ethyleneglycol, propanediol, butanediol, pentanediol, or hexandiol is used as an initiator, 2-arm polylactic acid is formed; glycerol as an initiator, 3-arm polylactic acid; erythritol, pentaerythritol, or threitol as an initiator, 4-arm polylactic acid; adonitol or sorbitol as an initiator, 5-arm polylactic acid; sorbitol or mannitol as an initiator, 6-arm polylactic acid; and disaccharide or trisaccharide as an initiator, more than 7-arm polylactic acid is synthesized.

In the step 2), polylactic acid obtained in step 1) is dissolved in water-miscibile organic solvent, followed by removing unreacted linear polylactic acid. It is preferable to use acetone, acetonitrile, etc., as water-miscibile organic solvent.

Linear polylactic acids that do not react with the initiator are removed by dissolving them in neutral or alkali aqueous solution of pH 7 or more. Neutral or alkali aqueous solution of pH 7 or more is not limited specially, but is preferable to use sodium hydrogen carbonate aqueous solution. After performing such purifying procedure more than 2 times, polymer is washed with distilled water, dried in vacuum, to obtain powder form of branched polylactic acid.

In the step 3), carboxy group is introduced to hydroxy terminal of the branched polylactic acid by adding succinic anhydride or dichloride compound such as oxalyl chloride, malonyl chloride, glutaryl chloride, succinyl chloride, adipoyl chloride, sebacoyl chloride, dodecadioyl dichloride etc. Preferably, succinic anhydride is used. It is also preferable to perform the reaction in sealed condition for more than 6 hours.

It is preferable that succinic anhydride or dichloride compound used in the reaction is added in about 1-2 fold of the mole of terminal hydroxy group of polylactic acid derivative. Thus formed branched polylactic acid derivative is dissolved in acetone and precipitated in distilled water, and thus precipitated polymer is filtered, washed with distilled water again, placed in distilled water, and dissolved completely at 50-70° C. while adding a small amount of sodium hydrogen carbonate. Not reacted polymers are removed by filtration since they are not dissolved. To completely dissolved polymer aqueous solution, 1 N hydrochloric acid aqueous solution is added bit by bit, to precipitate resulting polymer. Thus precipitated polymer is washed with distilled water for more than 3 times, dried in vacuum, to obtain the branched polylactic acid derivative containing carboxy terminal group (multi-arm PLA-COOH). The branched polylactic acid derivative containing this carboxy terminal group has carboxy terminal groups at each branch.

Further, in the step 4), the polylactic acid derivative obtained in the step 3) is dissolved in acetone or acetone aqueous solution, and then an metal ion salt such as sodium hydrogen carbonate, sodium carbonate, potassium hydrogen carbonate, potassium carbonate, lithium carbonate, etc. is add thereto bit by bit for neutralization, to obtain metal ion salt form of the branched polylactic acid derivative by evaporating solvent.

The branched polylactic acid derivative of the present invention can form polymer micelles in aqueous solution of pH 4 or more, and so can be used as poorly soluble drug delivery agent. That is, to administer poorly soluble drugs orally or parenterally to human body, micelles are formed in aqueous solution of more than pH 4 by using the polylactic acid derivative of the present invention, and then poorly soluble drug can be contained and solubilized inside the micelles formed. When polymer micelles containing poorly soluble drug are administered to human body, poorly soluble drugs are released slowly and exhibit pharmacological effect, with maintaining stable state inside the micelles formed by the polylactic acid derivative.

Poorly water-soluble drugs capable of solubilization by using the polylactic acid derivative of the present invention may be any poorly water-soluble drug which has the water solubility of 10 mg/ml or less. Representative poorly water-soluble drugs are paclitaxel, ketoconazole, itraconazole, cyclosporine, cisapride, acetaminophen, aspirin, acetyl salicylic acid, indomethacin, naproxen, warfarin, papaverine, thiabendazole, miconazole, cinnarizine, doxorubicin, omeprazole, cholecalciferol, melphalan, nifedipine, dioxin, benzoic acid tryptophan, tyrosine, phenyl alanine, aztreonam, ibuprofen, phenoxymethylpenicillin, thalidomide, methyl testosterone, proclorperazine, hydrocortisone, dideoxypurine nucleoside, vitamin D2, sulfonamide, sulfonylurea, para-aminobenzoic acid, melatonin, benzyl penicillin, chlorambucil, diazepine, digitoxin, hydrocortisone butyrate, metronidazole benzoate, tolbutamide, prostaglandin, fludrocortisone, griseofulvin, miconazole nitrate, leukotriene B4 inhibitor, propranolol, theophylline, flurbiprofen, sodium benzoate, benzoic acid, riboflavin, benzodiazepine, phenobarbital, glyburide, sulfadiazine, sulfoethyl thiadiazole, diclofenac sodium, phenyloin, thioridazine hydrochloride, bropirimine, hydrochlorothiazide, fluconazole, etc. In addition, other poorly soluble drugs used as antibiotics, anti-inflammatory analgesics, anesthetics, hormones, antihypertensive agents, and agents for the treatment of diabetes, antihyperlipidemic agents, antiviral agents, agents for the treatment of Parkinson's disease, antidementia agents, antiemetics, immunosuppressants, antiulcerative agents, laxatives, and antimalarial agents are included.

To entrap the above poorly soluble drug into micelles formed by the polylactic acid derivative, the polylactic acid derivative of 80.0-99.9% by weight and poorly soluble drug of 0.1-20.0% by weight are added.

The branched polylactic acid derivative of the present invention can be prepared in the form of micelles containing poorly soluble drug and be administered orally or parenterally. In parenteral administration, poorly soluble drug is injected by vascular, subcutaneous, or muscular routes, etc., and particularly the above polylactic acid derivative is injected in mixture with the poorly soluble drug intramuscularly or subcutaneously. Also, the oral administration is conducted by mixing the branched polylactic acid derivative of the present invention with the poorly soluble drug and preparing in the form of tablet or capsule. Also, in parenteral administration, the dosage forms are prepared to form micelles in the body fluid of pH 6-7, and in oral administration, the dosage forms are prepared to solubilize in the form of micelles and release drug at the intestine of pH 6-7, not to release drug in the stomach of pH 1-2.

Upon oral administration, the pharmaceutical compositions containing poorly soluble drug of the present invention are moved from the stomach to the intestine. The pH of stomach is lower than the pH of intestine, and polylactic acid contained in the pharmaceutical compositions of the present invention is maintained in the form of tablet or capsule and not released in lower pH. However, after moving to the intestine of pH 6-7 the pharmaceutical compositions are slowly solubilized into the form of micelles containing drug, and then the drug is released and absorbed at the intestine. These properties enhance the stability of drug by inhibiting release of unstable drug in low pH solution. In case of anti-inflammatory analgesics, etc. which are released in solution of pH 1-2 to have side effects such as gastric ulcer, etc., these properties provide advantages to decrease side effects of drug and to increase pharmacological effects by being released in the intestine of pH 6-7, not in the stomach.

The preparation method of micelles containing the poorly soluble drug using the branched polylactic acid derivative of the present invention is as follows.

The branched polylactic acid derivative of the present invention and poorly soluble drug are dissolved in acetone, acetic acid ethyl, acetonitrile, dichloromethan, ethanol, methanol, chloroform, or acetic acid, and organic solvent is removed therefrom, to prepare uniform mixture of the polylactic acid derivative and poorly soluble drug. To thus obtained mixture is added distilled water, and the pH of aqueous solution is adjusted to pH 4-8, automatically to form micelles containing drug. The micelles aqueous solution containing poorly soluble drug can be lyophilized.

Also, to prepare as oral dosage form, the above polylactic acid derivative and poorly soluble drug are dissolved in organic solvent, solvent is removed therefrom, and thus resulting mixture of the polylactic acid derivative and poorly soluble drug is mixed with oral excipient to prepare tablet or to fill in capsule.

As shown in the Example of the present invention, the size of micelles is 10-50 nm and the solubility of the poorly soluble drug is 15-35 mg/ml from solubilization experiment by using paclitaxcel as a poorly soluble drug, Below, the present invention is more specifically explained by the Example and experimental embodiment. It should nevertheless be understood that they are not intended to limit the scope of the invention in any way.

Preparation Example 1

Synthesis of 3-Arm PLA-OH (Mn~3,000)

Glycerol (1 g; 0.011 mol) was put into 100 ml of flask having stop cock., which was put into oil bath heated to 80° C., and moisture was removed therefrom under vacuum condition for 30 minutes.

Tin octoate as catalyst was added hereto in the amount of 0.1 wt % of lactide after dissolved in toluene. In vacuum, toluene was removed, and lactide (35.8 g; 0.249 mol) was added thereto, which is shaken by using magnetic bar until lactide is completely melted. Then, the interior of reactor was sealed in vacuum. The polymerizing temperature is set at 125-130° C., and then polymerization was performed under vacuum condition for about 6 hours. Thus synthesized polymer was dissolved in acetone. To the acetone solution that the polymer was completely dissolved, sodium hydrogen carbonate aqueous solution (0.2N) was added bit by bit, which was adjusted to pH 7-8 and stirred, to precipitate polymer.

Thus precipitated polymer was washed with distilled water 3-4 times, and dried in vacuum to obtain powder form of 3-arm PLA-OH (31 g, yield: 95%). The number average molecular weight of thus obtained polymer was determined as 2,969 Dalton by $^1$H-NMR spectrum (FIG. 1).

Preparation Example 2

Synthesis of 3-Arm PLA-OH (Mn~1,000)

3-arm PLA-OH (29.5 g, yield: 91%) was obtained according to the same procedure as in Preparation Example 1 except that 3 g of glycerol was used.

Preparation Example 3

Synthesis of 3-Arm PLA-OH (Mn~2,000)

3-arm PLA-OH (30 g, yield: 92%) was obtained according to the same procedure as in Preparation Example 1 except that 1.5 g of glycerol was used.

Preparation Example 4

Synthesis of 3-Arm PLA-OH (Mn~4,000)

3-arm PLA-OH (30 g, yield: 92%) was obtained according to the same procedure as in Preparation Example 1 except that 0.75 g of glycerol was used.

Preparation Example 5

Synthesis of 5-Arm PLA-OH (Mn~4,000)

5-arm PLA-OH (25 g, yield: 95%) was obtained according to the same procedure as in Preparation Example 1 except that xylitol (1 g, 0.007 mol) and lactide (29 g) were used.

Example 1

Synthesis of 3-Arm PLA-COOH (Mn~3,000)

Figure 2:
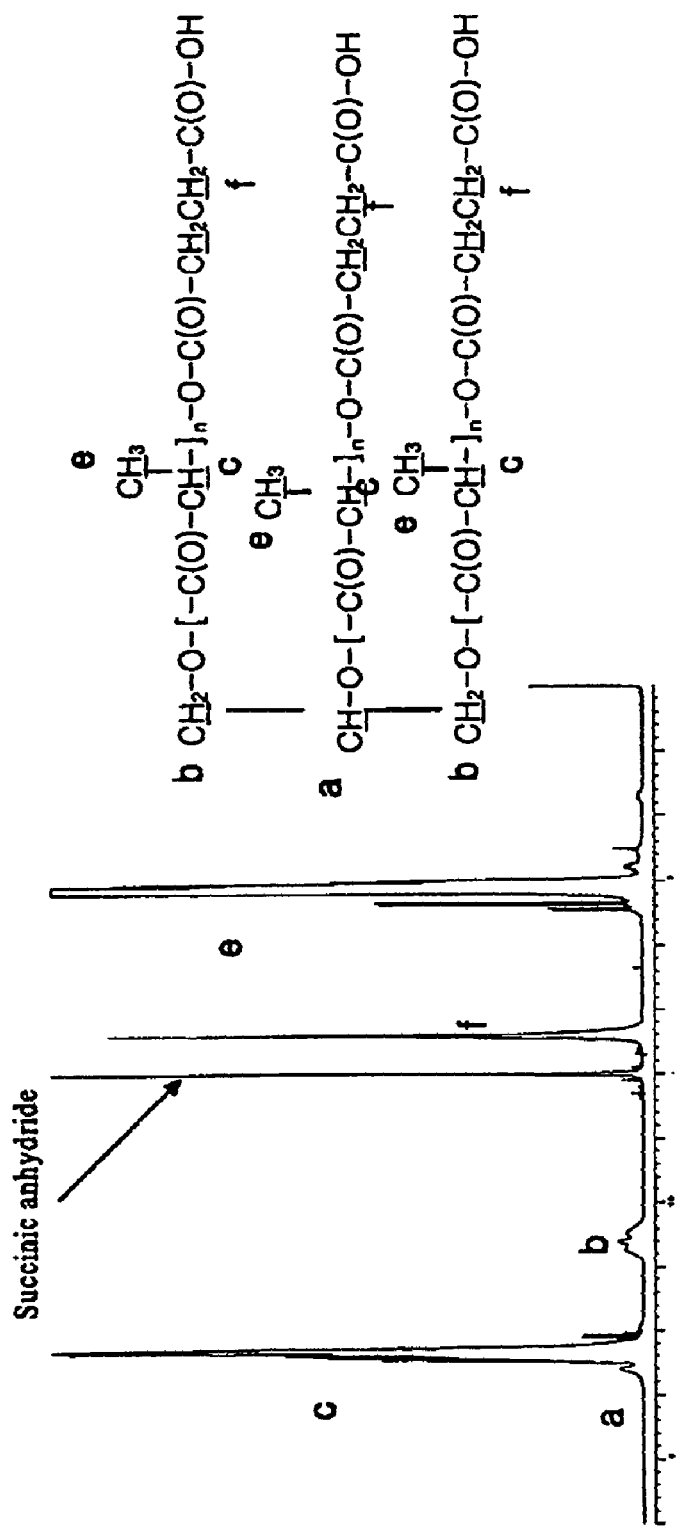
FIG. 2 is $^1$H-NMR spectrum of 3-arm PLA-COOH (Example 1)

3-arm PLA-OH (100 g; 0.033 mol) synthesized in Preparation Example 1 was introduced into 1-neck flask, and moisture contained in the polymer was completely removed at 125° C. under vacuum condition for 1 hour. For the hydroxy terminal group mole of polymer [0.033×3(number of branch)= 0.099 mol], succinic anhydride (19.8 g; 0.198 mol) was added, then the reactor was sealed, and reacted at the reaction temperature of 125° C. for 6 hours. To thus obtained acetone solution in which polymer was dissolved was added distilled water bit by bit to precipitate the polymer. The precipitated polymer was completely dissolved in sodium hydrogen carbonate aqueous solution at 60° C. Non-dissolved part therein, if any, was filtered to remove. Hydrochloric acid (1 N) aqueous solution was added bit by bit to precipitate 3-arm PLA-COOH. Thus obtained polymer was washed with water 3 times, and dried in vacuum. The number average molecular weight of thus obtained 3-arm PLA-COOH was determined as 3,108 Dalton by $^1$H-NMR spectrum (FIG. 2).

Example 2

Synthesis of 3-Arm PLA-COOH (Mn~1,000)

3-arm PLA-COOH was obtained according to the same procedure as in Example 1 except that 3-arm PLA-OH (33 g) synthesized in Preparation Example 2 was used.

Example 3

Synthesis of 3-Arm PLA-COOH (Mn~2,000)

3-arm PLA-COOH was obtained according to the same procedure as in Example 1 except that 3-arm PLA-OH (66 g) synthesized in Preparation Example 3 was used.

Example 4

Synthesis of 3-Arm PLA-COOH (Mn~4,000)

3-arm PLA-COOH was obtained according to the same procedure as in Example 1 except that 3-arm PLA-OH (132 g) synthesized in Preparation Example 4 was used.

Example 5

Synthesis of 5-Arm PLA-COOH (Mn~4,000)

5-arm PLA-COOH was obtained according to the same procedure as in Example 1 except that 5-arm PLA-OH (80 g) synthesized in Preparation Example 5 was used.

Example 6

Synthesis of 3-Arm PLA-COONa (Mn~3,000)

3-arm PLA-COOH synthesized in Example 1 was dissolved in acetone, which was introduced into round-bottom flask, and then slowly stirred at room temperature after equipping shaker. Sodium hydrogen carbonate aqueous solution (1 N) was slowly added hereto for neutralization. A small amount of acetone solution was diluted with plenty of distilled water, and confirmed the solution to have pH 7, then excess of moisture was removed by adding anhydrous magnesium sulfate, which was filtered and evaporated acetone by solvent evaporator, to obtain white solid. This white solid was dissolved in anhydrous acetone again, and non-dissolving material was removed by filtering, and then acetone was evaporated, to obtain 3-arm PLA-COONa in white solid form.

Figure 3:
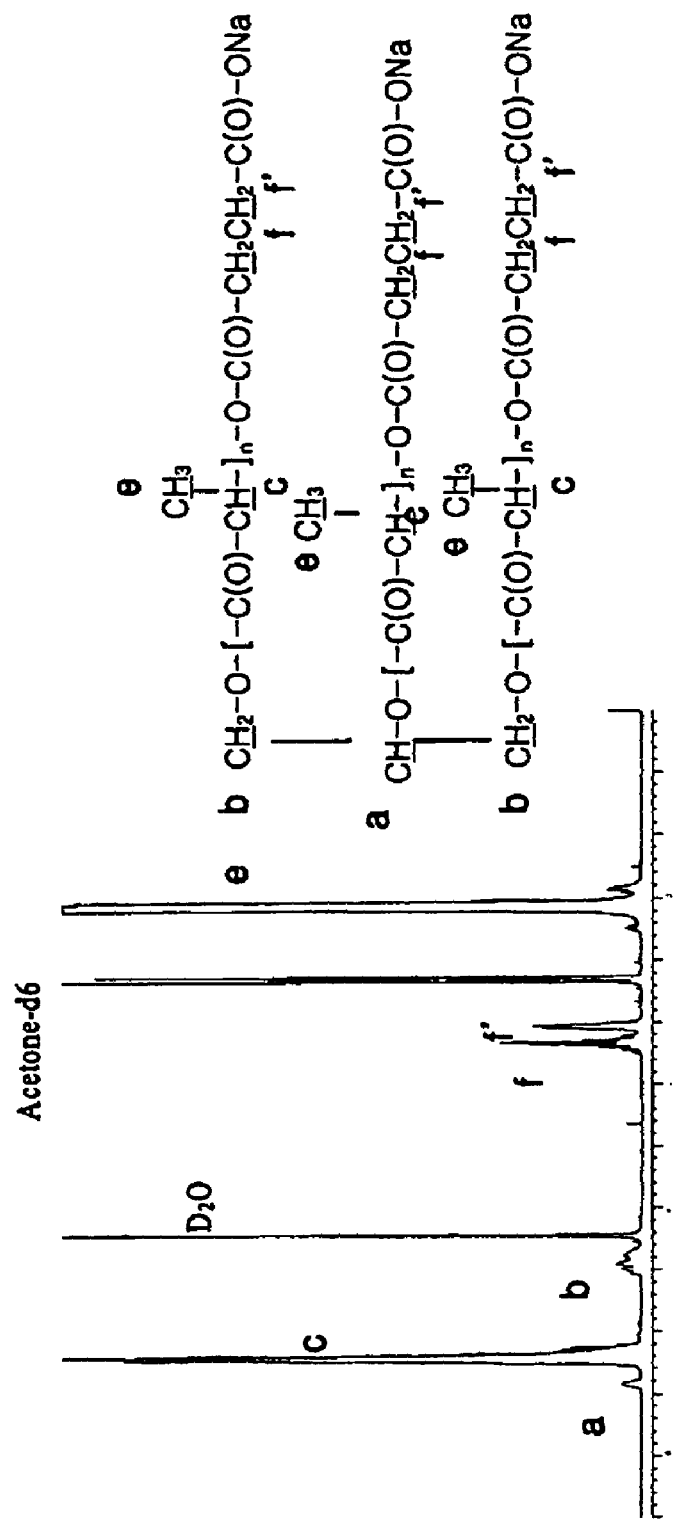
FIG. 3 is $^1$H-NMR spectrum of 3-arm PLA-COONa (Example 6)

The number average molecular weight of thus obtained 3-arm PLA-COONa was determined as 3,085 Dalton by $^1$H-NMR spectrum (FIG. 3).

Example 7

Synthesis of 3-Arm PLA-COONa (Mn~1,000)

3-arm PLA-COONa was obtained according to the same procedure as in Example 6 except that 3-arm PLA-COOH synthesized in Example 2 was used.

Example 8

Synthesis of 3-Arm PLA-COONa (Mn~2,000)

3-arm PLA-COONa was obtained according to the same procedure as in Example 6 except that 3-arm PLA-COOH synthesized in Example 3 was used.

Example 9

Synthesis of 3-Arm PLA-COONa (Mn~4,000)

3-arm PLA-COONa was obtained according to the same procedure as in Example 6 except that 3-arm PLA-COOH synthesized in Example 4 was used.

Example 10

Synthesis of 5-Arm PLA-COONa (Mn~4,000)

5-arm PLA-COONa was obtained according to the same procedure as in Example 6 except that 5-arm PLA-COOH synthesized in Example 5 was used.

Preparation Example 6

Synthesis of 3-Arm PLGA-OH (Mn~3000)

3-arm PLGA-OH was obtained according to the same procedure as in Preparation Example 1 except that lactide (20.2 g; 0.14 mol) was used with glycolide (16.3 g, 0.14 mol).

Example 11

Synthesis of 3-Arm PLGA-COOH (Mn~3,000)

3-arm PLGA-COOH was obtained according to the same procedure as in Example 1 except that 3-arm PLGA-OH (100 g) synthesized in Preparation Example 6 was used.

Example 12

Synthesis of 3-Arm PLGA-COONa (Mn~3,000)

3-arm PLGA-COONa was obtained according to the same procedure as in Example 6 except that 3-arm PLGA-COOH synthesized in Example 11 was used.

Example 13

Synthesis of 3-Arm PLA-COOH (Mn~3,000)

3-arm PLA-OH (100 g; 0.033 mol) synthesized in Preparation Example 1 was introduced into 1-neck flask, and moisture contained in the polymer was completely removed at 125° C. under vacuum condition for 1 hour. The dried polymer was completely dissolved in 200 ml of acetone and the reaction temperature was set to 50° C. For the hydroxy terminal group mole of polymer [0.033×3(number of branch) =0.099 mol], succinic chloride (55 ml; 0.495 mol) was added. With inflow of $N_2$ into the reactor, the reaction was conducted for 12 hours. The acetone solution in which thus obtained polymer was dissolved was added to distilled water bit by bit to precipitate the polymer. Thus precipitated polymer was washed with distilled water, and then completely dissolved in sodium hydrogen carbonate aqueous solution at 60° C. Non-dissolved part was filtered to remove. Hydrochloric acid (1 N) aqueous solution was added hereto bit by bit to precipitate 3-arm PLA-COOH. Thus obtained polymer was washed with water 3 times, and dried in vacuum.

Comparison Example 1

Synthesis of Sodium Salt of Linear Polylactic Acid (D,L-PLA-COONa)

(1) Synthesis 1 of D,L-Polylactic Acid (PLA-COOH)

100 g of D,L-lactic acid was introduced into a 250 ml 3-neck round-bottomed flask, and the flask was equipped with a stirrer, and heated in an oil bath to 80° C. The reaction was performed for 1 hour with reducing the pressure to 25 mmHg by a vacuum aspirator to remove excessive moisture. With increasing the reaction temperature to 160° C., the pressure was reduced to 10 mmHg, and the reaction was conducted for 12 hours, and then stopped. To the resulting reactant was added 1 L of distilled water to precipitate polymer. Thus precipitated polymer was added to distilled water to remove low molecular weight of oligomers which are dissolved in a solution of pH 4 and less, and thus precipitated polymer was added to 1L of distilled water. Sodium hydrogen carbonate solution was added thereto bit by bit for the solution to reach pH 6-8, to dissolve polymer completely thereby. At this time, non-water soluble polymer was removed by centrifugation, filtration, etc.

While adding 1 N hydrochloric acid aqueous solution bit by bit to adjust the aqueous solution to pH 2, polymer was precipitated from the aqueous solution. Thus precipitated polymer was washed with distilled water 2 times, isolated, and dried under reduced pressure to obtain non-crystalline oligomer (D,L-polylactic acid 66 g, yield: 66%). Thus obtained number average molecular weight was 1,140 Dalton.

(2) Synthesis 1 of the Sodium Salt of Linear Polylactic Acid (PLA-COONa)

D,L-polylactic acid (number average molecular weight: 1,140 Dalton) synthesized in Comparison Example 1 (1) was dissolved in acetone, which was introduced into a round-bottomed flask, and a stirrer was added thereto. The solution was slowly stirred at room temperature, and sodium hydrogen carbonate aqueous solution (1 N) was slowly added thereto for neutralization.

A small amount of acetone solution was diluted with plenty of distilled water, and it was confirmed that the solution has pH 7. Then, excess of moisture was removed therefrom by adding anhydrous magnesium sulfate, and the reaction was filtered and acetone was evaporated therefrom by solvent evaporator, to obtain white solid. The white solid was dissolved in anhydrous acetone and the reaction was filtered to remove material which was not dissolved in anhydrous acetone, and acetone was evaporated therefrom, to obtain sodium salt of D,L-polylactic acid (yield: 96%) in white solid form.

Comparison Example 2

Synthesis of Sodium Salt of Linear Polylactic Acid (D,L-PLA-COONa)

(1) Synthesis 2 of D,L-Polylactic Acid (PLA-COOH)

75 g of D,L-polylactic acid (yield: 75%) was obtained according to the same procedure as in Comparison Example 1 (1) except that the reaction was performed for 24 hours under the condition that temperature was increased to 160° C. and the pressure was reduced to 5 mmHg. The number average molecular weight was 2,500 Dalton.

(2) Synthesis 2 of Sodium Salt of Polylactic Acid (PLA-COONa)

Sodium salt of polylactic acid (yield: 95%) was synthesized according to the same procedure as in Comparison Example 1 (2) except that D,L-polylactic acid (the number average molecular weight: 2,500 Dalton) was synthesized in Comparison Example 2 (1) was used.

Experimental Example 1

Micelles Formation According to the Molecular Weight

Each sodium salt of 3-arm branched polylactic acid having the number average molecular weights of 1,000, 2,000, 3,000, and 4,000 Dalton was dissolved in distilled water, and then the particle size of formed micelles was determined by using DLS (dynamic light scattery, ZetaPlus, Brookhaven Instruments Corp.). The results for particle size are shown in Table 1.

TABLE 1

|  | Polymer (molecular weight) | Average size of micelles (nm) | polymer aqueous solution concentration (mg/ml) | CMC (µg/ml) |
|---|---|---|---|---|
| Comparison Example 1 | D,L-PLA-COONa(1,140) | 15 | 20 | 2 |
| Comparison Example 2 | D,L-PLA-COONa(2,500) | Could not determined | 20 | — |
| Example 6 | 3-arm PLA-COONa(3,000) | 22 | 20 | 0.75 |
| Example 7 | 3-arm PLA-COONa(1,000) | 10 | 20 | 10 |
| Example 8 | 3-arm PLA-COONa(2,000) | 14 | 20 | 1 |
| Example 9 | 3-arm PLA-COONa(4,000) | 26.3 | 20 | 0.5 |

As shown in Table 1, in the case of D,L-PLA-COONa of Comparison Example 2, the size of micelle could not be determined since it was not dissolved in water. Like this, the linear polylactic acid metal salt has one carboxy group acting as hydrophilic, and so become water-insoluble polymer due to increase of hydrophobicity if the molecular weight of hydrophobic part is over the limitation value (about 2,000). However, the branched polymer of Example 6 and Example 9 have several carboxy groups, and so are dissolved in water to form micelles though the molecular weight is increased, and the size of formed micelles is larger than that of Comparison Example 1.

Also, it is shown that the higher polymeric molecular weight is, the lower CMC value is, which means that higher molecular weight can form stable micelles in aqueous solution.

In case of linear polylactic acid derivatives, the polymeric molecular weight capable of forming micelles is 2,000 Dalton at the maximum. However, in case of branched polylactic acid derivatives, more stable micelles can be formed since the maximum molecular weight of 18,000 Dalton can form micelles in aqueous solution.

Experimental Example 2

Solubilization Test of Poorly Soluble Drug

The sodium salt of branched polylactic acid synthesized in the above Examples and paclitaxcel were dissolved in each of organic solvent of acetone, ethanol, acetic acid ethyl, acetonitrile, dichloromethane, and chloroform, to prepare clear solutions, and organic solvent was removed therefrom by vacuum evaporator, to prepare uniform mixture of poorly drug and oligomer. They were dissolved in distilled water. Thus resulted micelles aqueous solutions containing poorly soluble drugs were filtrated by using membrane filter having 200 nm of pore size to remove non-dissolved drugs, and then the drugs concentrations in aqueous solution were quantified by liquid chromatography. The results are shown in Table 2.

TABLE 2

| Polymer (molecular weight) | Poorly soluble drug | Composition ratio of drug (%) | Size of micelles (nm) | Solubility of drug (mg/ml) |
|---|---|---|---|---|
| PLA-COONa(1,140) | paclitaxcel | 5 | 14 | 25 |
| PLA-COONa(1,140) | paclitaxcel | 10 | 24 | 20 |
| PLA-COONa(1,140) | paclitaxcel | 15 | 30 | 15 |
| 3-arm PLA-COONa(3,000) | paclitaxcel | 10 | 33 | 27 |
| 3-arm PLA-COONa(2,000) | paclitaxcel | 10 | 25 | 22 |
| 3-arm PLA-COONa(4,000) | paclitaxcel | 10 | 39 | 32 |

As showed in Table 2, it is confirmed that the branched polylactic acid metal salt of the present invention can effectively solubilize the representative poorly soluble drug, paclitaxcel. That is, paclitaxcel of poorly soluble drug has water solubility of 0.01 mg/ml or less, but in case of using branched polylactic acid metal salt of the present invention, a large amount of drugs of 15-35 mg/ml may be solubilized as micelles form, and so a large amount of drugs can be stably administrated into the body.

Experimental Example 3

Solubility of Branched Polylactic Acid Derivatives According to pH

In order to measure solubility of the sodium salt of branched polylactic acid synthesized in Example 9 according to pH, the sodium salt of branched polylactic acid was dissolved in aqueous solution adjusted to pH 2 by using hydrochloric acid (1 N) aqueous solution and distilled water, then to observe the aqueous solution. The results are shown in FIG. 4.

Figure 4:
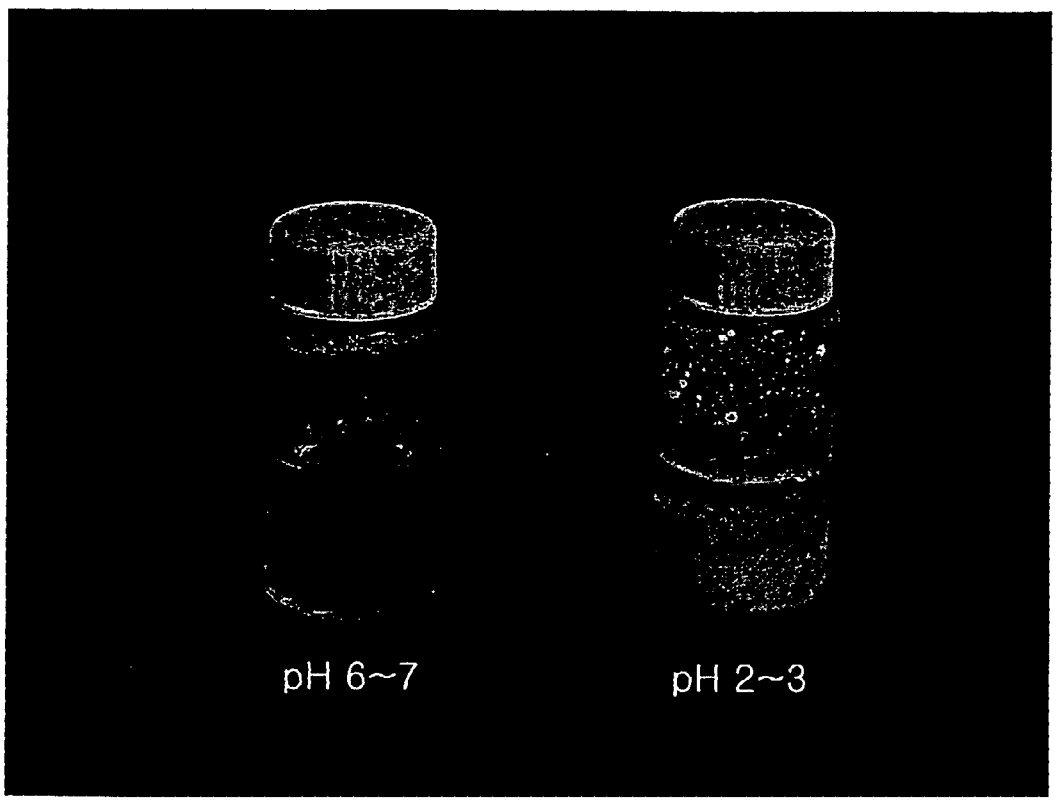
FIG. 4 shows the solubility of 3-arm PLA-COONa according to pH.

As shown in FIG. 4, in the range of pH 2-3, it is confirmed that the branched polylactic acid derivatives solution was not solibilized, and so polymer was precipitated therein. In the range of pH 6-7 which is similar to that of the body fluid, it is confirmed that branched polylactic acid derivatives were solibilized, and so clear fluid was formed therein. Also, it was determined that exhibiting the light blue color is due to micelles which formed in aqueous solution.

Utility of Technical Field

As shown above, branched polylactic acid derivatives of the present invention, of which one terminal is carboxy acid or carboxy acid alkali metal salt form and the number average molecular weight is 1,000 Dalton, can be solubilized in aqueous solution of more than pH 4 to form micelles by forming balance between hydrophilic and hydrophobic group. The size of formed micelles is 10-50 nm, and so they are preferable as delivery agent of poorly soluble drug. Polylactic acid derivatives of the present invention have branched structure containing several hydrophilic terminal groups, even high molecular weight of polylactic acid can be solubilized in aqueous solution. Also, these micelles containing poorly soluble drug may be applied to various forms of drug delivery agent.

What is claimed is:

1. A micellar composition comprising a branched polylactic acid derivative of formula (I) for forming micelles in an aqueous solution with a pH of 4 or more:

$$I-(R-X)_n \qquad (1)$$

Wherein,

R is —[R$_1$]$_k$—[R$_2$]$_m$—, wherein R$_1$ is —C(=O)—CHZ—O—,

R$_2$ is selected from the group consisting of —C(=O)—CHY—O—, —C(=O)—CH$_2$CH$_2$CH$_2$CH$_2$CH$_2$—O— and —C(=O)—CH$_2$—O—CH$_2$CH$_2$—O—, wherein each of Z and Y is selected from the group consisting of hydrogen, methyl, and phenyl, k is an integer of 1-30, m is an integer of 0-30;

X is —C(=O)—(CH$_2$)$_a$—C(=O)—O-M, wherein a is an integer of 0-10, M is selected from the group consisting of hydrogen, sodium, potassium, and lithium;

I is a diol or a polyol having 3-12 hydroxy groups;

n is the same as the number of hydroxy groups that I has, and wherein I is selected from the group consisting of ethylene glycol, propanediol, butanediol, pentanediol, hexanediol, glycerol, erythritol, threitol, pentaerythritol, xylitol, adonitol, sorbitol, mannitol, disaccharide and trisaccharide, and wherein the branched polylactic acid derivative has a number average molecular weight of 1,000-18,000 Dalton.

2. The micellar composition according to claim 1, wherein R is mono polymer or copolymer which is one or more selected from the group consisting of lactide, glycolide, caprolactone, 1,4-dioxane-2-one, and mandelic acid.

3. The micellar composition according to claim 1, wherein M is sodium, potassium or lithium.

4. The micellar composition according to claim 1, wherein the disaccharide is selected from the group consisting of palatinose, maltose monohydrate and maltitol, and the trisaccharide is D-raffinose pentahydrate.

5. A method of preparing the polylactic acid derivative described in any one of claims 1 and 2 to 4, comprising the steps of
1) polymerizing a monomer of lactides in the presence of an initiator and a catalyst to obtain a branched polylactic acid;
2) dissolving the branched polylactic acid obtained in step 1) in a water-miscibile organic solvent, purifying the branched polylactic acid by adding an aqueous solution with a pH of 7 or more, and drying in vacuum, to obtain a powder form of the branched polylactic acid; and
3) reacting the branched polylactic acid derivative obtained in step 2) with succinic anhydride or a dichloride compound to obtain the branched polylactic acid derivative containing terminal carboxy group, wherein the initiator of step 1) is selected from the group consisting of ethylene glycol, propanediol, butanediol, pentanediol, hexanediol, glycerol, erythritol, threitol, pentaerythritol, xylitol, adonitol, sorbitol, mannitol, disaccharide and trisaccharide, and wherein the branched polylactic acid derivative has a number average molecular weight of 1,000-18,000 Dalton.

6. The method according to claim 5, further comprising the step of adding an alkali metal salt to the branched polylactic acid derivative obtained in step 3) to obtain the branched polylactic acid derivative containing carboxy alkali metal salt terminal group.

7. The method according to claim 5, wherein the disaccharide is selected from the group consisting of palatinose, maltose monohydrate and maltitol, and the trisaccharide is D-raffinose pentahydrate.

8. The method according to claim 5, wherein in step 3, the branched polylactic acid derivative is reacted with a compound which is selected from the group consisting of succinic anhydride, oxalyl chloride, malonyl chloride, succinyl chloride, glutaryl chloride, adipoyl chloride, sebacoyl chloride, and dochecadioyl dichloride.

9. The method according to claim 6, wherein the alkali metal salt is selected from the group consisting of sodium hydrogen carbonate, sodium carbonate, potassium hydrogen carbonate, potassium carbonate, and lithium carbonate.

10. The micellar composition according to any one of claims 1 and 2-4, wherein said composition is for a poorly, water-soluble drug delivery agent.

11. A pharmaceutical composition containing the polylactic acid derivative described in any one of claims 1 and 2 to 4 and a poorly, water-soluble drug.

12. The micellar composition according to claim 1, wherein said branched polylactic acid derivative entrap drugs in the micelles by forming stable micelles in aqueous solution and solubilizing poorly water-soluble drugs within the micelles.

* * * * *